United States Patent
Anifowose et al.

(10) Patent No.: US 11,010,883 B2
(45) Date of Patent: May 18, 2021

(54) AUTOMATED ANALYSIS OF PETROGRAPHIC THIN SECTION IMAGES USING ADVANCED MACHINE LEARNING TECHNIQUES

(71) Applicant: Saudi Arabian Oil Company, Dhahran (SA)

(72) Inventors: Fatai A. Anifowose, Dhahran (SA); Mokhles Mustapha Mezghani, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 150 days.

(21) Appl. No.: 15/955,072

(22) Filed: Apr. 17, 2018

(65) Prior Publication Data
US 2019/0318467 A1    Oct. 17, 2019

(51) Int. Cl.
*G06T 7/00* (2017.01)
*G06T 7/90* (2017.01)
(Continued)

(52) U.S. Cl.
CPC .......... *G06T 7/0002* (2013.01); *G06K 9/6218* (2013.01); *G06T 7/11* (2017.01);
(Continued)

(58) Field of Classification Search
CPC . G06T 7/0002; G06T 7/62; G06T 7/11; G06T 7/90; G06T 2207/30181;
(Continued)

(56) References Cited

U.S. PATENT DOCUMENTS

| 4,783,751 A | 11/1988 | Ehrlich |
| 4,868,883 A | 9/1989 | Chen |

(Continued)

OTHER PUBLICATIONS

Dey, "Fluvial Hydrodynamics," GeoPlanet: Earth and Planetary Science, 2014, 706 pages.
(Continued)

*Primary Examiner* — John W Lee
(74) *Attorney, Agent, or Firm* — Fish & Richardson P.C.

(57) ABSTRACT

Methods, systems, and apparatus, including computer programs encoded on a computer storage medium, for automated analysis of petrographic thin section images. In one aspect, a method includes determining a first image of a petrographic thin section of a rock sample, and determining a feature vector for each pixel of the first image. Multiple different regions of the petrographic thin section are determined by clustering the pixels of the first image based on the feature vectors, wherein one of the regions corresponds to grains in the petrographic thin section. The method further includes determining a second image of the petrographic thin section, including combining images of the petrographic thin section acquired with plane-polarized light and cross-polarized light. Multiple grains are segmented from the second image of the petrographic thin section based on the multiple different regions from the first image, and characteristics of the segmented grains are determined.

20 Claims, 5 Drawing Sheets

(51) Int. Cl.
*G06T 7/11* (2017.01)
*G06T 7/62* (2017.01)
*G06K 9/62* (2006.01)

(52) U.S. Cl.
CPC .................. *G06T 7/62* (2017.01); *G06T 7/90* (2017.01); *G06T 2207/10056* (2013.01); *G06T 2207/10152* (2013.01); *G06T 2207/20081* (2013.01); *G06T 2207/20152* (2013.01); *G06T 2207/20221* (2013.01); *G06T 2207/30181* (2013.01)

(58) Field of Classification Search
CPC . G06T 2207/10152; G06T 2207/20081; G06T 2207/20152; G06T 2207/10056; G06T 2207/20221; G06T 7/174; G06T 7/0004; G06T 2207/30242; G06T 2207/10024; G06K 9/6218; G06K 9/4652; G06K 9/2036; G01N 33/241; G02B 21/0092; G02B 21/365
See application file for complete search history.

(56) References Cited

U.S. PATENT DOCUMENTS

| | | | |
|---|---|---|---|
| 6,205,402 B1 | 3/2001 | Lazaar et al. | |
| 6,246,963 B1 | 6/2001 | Cross et al. | |
| 6,754,588 B2 | 6/2004 | Cross et al. | |
| 7,424,367 B2 | 9/2008 | Saltzer et al. | |
| 8,583,410 B2 | 11/2013 | Sisk et al. | |
| 9,372,943 B2 | 6/2016 | Li et al. | |
| 9,626,771 B2 * | 4/2017 | Mezghani | G06T 3/60 |
| 2007/0133866 A1 * | 6/2007 | Chang | G06K 9/00 382/159 |
| 2008/0187219 A1 * | 8/2008 | Chen | H04N 7/18 382/173 |
| 2009/0164186 A1 | 6/2009 | Haase et al. | |
| 2009/0204377 A1 | 8/2009 | Van Wagoner et al. | |
| 2011/0295580 A1 | 12/2011 | Sisk | |
| 2015/0127261 A1 | 5/2015 | Aldea et al. | |
| 2015/0234863 A1 * | 8/2015 | Lilje | G06K 9/00637 382/103 |
| 2015/0293257 A1 | 10/2015 | Liebich et al. | |
| 2016/0343150 A1 * | 11/2016 | Mezghani | G02B 21/361 |
| 2017/0091958 A1 * | 3/2017 | Mezghani | G06K 9/4604 |

OTHER PUBLICATIONS

Hoogendoorn et al., "Storms: Process-response modelling of fluvio-deltaic stratigraphy," Computers and Geosciences vol. 34, Issue 10, Oct. 2008, 23 pages.
Kubo et al., "Advance and application of the stratigraphic simulation model 2D-SedFlux: From tank experiment to geological scale simulation," Sedimentary Geology, vol. 178, Issues 3-4, Jul. 15, 2005 9 pages.
opendtect.org' [online], "Open Seismic Repository," available on or before Dec. 7, 2017, [retrieved on Jun. 11, 2018], retrieved from URL: <http://opendtect.org/osr/>, 2 pages.
International Search Report and Written Opinion issued in International Application No. PCT/US2019/024755 dated Jul. 12, 2019, 12 pages.
International Search Report and Written Opinion issued in International Application No. PCT/US2016/029748 dated Aug. 5, 2016, 16 pages.
Benedet et al., "A morphological modeling study to compare different methods of wave climate schematization and evaluate strategies to reduce erosion losses from a beach nourishment project," Coastal Engineering, vol. 112, Jun. 2016, 18 pages.
Benedet et al., "Optimization of nearshore dredge pit design to reduce impacts on adjacent beaches," Journal of Coastal Research vol. 29, Issue 3, May 2013, 8 pages.
Bornholdt et al., "Experiments in Stratigraphy: Recent Advances in Stratigraphic and Sedimentologic Computer Simulators—Inverse stratigraphic modeling using genetic algorithms," SEPM Publication, Society of Sedimentary Geology, No. 62, Jan. 1, 1999, 6 pages.
Brown and Davies, "Methods for medium-term prediction of the net sediment transport by waves and currents in complex coastal regions," Continental Shelf Research, vol. 29, Jun. 2009, 13 pages.
Cantrell et al., "New tools and approaches in carbonate reservoir quality prediction: a case history from the Shu'aiba Formation, Saudi Arabia," The Geological Society of London, Special Publications, Sep. 29, 2014, 25 pages.
Cazanacli et al., "Deltaic Network Growth and Stratigraphy through a Rule Based Geometric Model," AAPG 2015, Annual Convention and Exhibition, May 31-Jun. 3, 2015, 48 pages.
Chatzirodou et al., "Investigation of deep sea shelf sandbank dynamics driven by highly energetic tidal flows," Marine Geology, vol. 380, Oct. 1, 2016, 19 pages.
Cross and Lessenger, "Construction and application of a stratigraphic inverse model," SEPM Special Publications, vol. 62, Jan. 1, 1999, 15 pages.
De Bruin and Bouanga, "Time attributes of Stratigraphic Surfaces, analyzed in the structural and Wheeler transformed domain," EAGE 69th Conference and Exhibition, Jun. 11-14, 2007, 5 pages.
Granjeon and Joseph, "Concepts and applications of a 3D multiple lithology, diffusive model in stratigraphic modeling," Numerical Experiments in Stratigraphy: Recent Advances in Stratigraphic and Sedimentological Computer Simulations, vol. 62, SEPM Special Publication, Jan. 1999, 15 pages.
Granjeon, "Modelisation stratigraphique deterministe: conception et applications d'un modele diffusif 3D multilithologique," Doctoral Thesis, Universit of Rennes 1, 1996, 216 pages.
Griffiths et al., "Sedsim in hydrocarbon exploration," Geologic Modeling and Simulation, Kluwer Academic, Jan. 2001, 27 pages.
Hoogendoorn, "The impact of changes in sediment supply and sea-level on fluvio-deltaic stratigraphy," PhD., Dissertation, Delft University of Technology, Jan. 31, 2006, 176 pages.
Huang et al., "Numerical forward modelling of 'fluxoturbidite' flume experiments using SEDSIM," Marine and Petroleum Geology vol. 35, Aug. 2012, 11 pages.
Huang et al., "Recent development in stratigraphic forward modelling and its application in petroleum exploration," Australian Journal of Earth Sciences, vol. 62, Issue 8, Jan. 2016, 18 pages.
Hutton and Syvitski, "Advances in the numerical modeling of sediment failure during the development of a continental margin," Marine Geology, vol. 203, Issue 3-4, Jan. 2004, 14 pages.
Hutton and Syvitski, "Sedflux 2.0: An advanced process-response model that generates three-dimensional stratigraphy," Computer and Geoscience vol. 34, Issue 10, Oct. 2008, 19 pages.
Kendall et al., "The simulation of the sedimentary fill of basins," Journal of Geophysical Research, vol. 96, No. B4, Apr. 10, 1991, 19 pages.
Kubo et al., "Inverse modeling of post Last Glacial Maximum transgressive sedimentation using 2D-SedFlux: Application to the northern Adriatic Sea," Marine Geology, vol. 234, Issues 1-4, Dec. 18, 2006, 11 pages.
Laigle et al, "A workflow integrating seismic interpretation and stratigraphic modelling—application to the NPRA Basin," EAGE Research Workshop: From Seismic Interpretation to Stratigraphic and Basin Modelling—Present and Future, Grenoble, Sep. 2006, 6 pages.
Lerche, "An inverse method for determining parameters for folded structures," Quarterly of applied mathematics, vol. 54, Dec. 1996, 11 pages.
Liang et al., "A reduced-complexity model for river delta formation—Part 1: Modeling deltas with channel dynamics," Earth Surface Dynamics vol. 3, Jan. 28, 2015, 20 pages.
Liang et al., "A reduced-complexity model for river delta formation—Part 2: Assessment of the flow routing scheme," Earth Surface Dynamics, vol. 3, Jan. 28, 2015, 18 pages.
Lorenzo-Trueba et al., "A geometric model for the dynamics of a fluvially dominated deltaic system under base-level change," Computers and Geosciences vol. 53, Apr. 2013, 9 pages.

(56) References Cited

OTHER PUBLICATIONS

Morehead et al, "Modeling the temporal variability in the flux of sediment from ungauged river basins," Global and Planetary Change, vol. 39, Issues 1-2, Oct. 2003, 16 pages.

Nicolas et al., "Forward Stratigraphic Modelling, Deterministic Approach to Improve Carbonate Heterogeneity Prediction; Lower Cretaceous, Abu Dhabi," International Petroleum Exhibition and Conference, Nov. 9-12, 2015, 16 pages.

Nordlund, "Formalizing geological knowledge with an example of modeling stratigraphy using fuzzy logic," Journal of Sedimentary Research vol. 66, Issue 4, Jul. 1, 1996, 10 pages.

Nordlund, "FUZZIM: forward stratigraphic modeling made simple," Computers and Geosciences, vol. 25, Issue 4, May 1999, 8 pages.

Overeem et al., "Three-dimensional numerical modeling of deltas," SEPM Special Issue, vol. 83, River Deltas: concepts, models and examples, Jan. 2005, 19 pages.

Pirmez et al., "Clinoform development by advection-diffusion of suspended sediment: Modeling and comparison to natural systems," Journal of Geophysical Research, vol. 103, Issue 24, Oct. 10, 1998, 18 pages.

Qayyum et al., "A modern approach to build 3D sequence stratigraphic framework," Oil and Gas Journal vol. 111, Oct. 2013, 16 pages.

Rafidah et al., "A review of stratigraphic simulation techniques and their applications in sequence stratigraphy and basin analysis," Bulletin of the Geological Society of Malaysia, vol. 54, Nov. 2008, 11 pages.

Ritchie et al., "Three-dimensional numerical modeling of deltaic depositional sequences 1: Influence of the rate and magnitude of sea-level change," Journal of Sedimentary Research, vol. 74, Issue 2, Mar. 1, 2004, 18 pages.

Ritchie et al., "Three-dimensional numerical modeling of deltaic depositional sequences 2: Influence of the rate and magnitude of sea-level change," Journal of Sedimentary Research, vol. 74, Issue 2, Mar. 1, 2004, 18 pages.

Seybold et al., "Modeling river delta formation," proceeding of the National Academy of the United States of America, vol. 104, Issue 43, Oct. 23, 2007, 6 pages.

Sharma, "Quantitative stratigraphic inversion," Dissertation for degree of Doctor of Philosophy in Geosciences, Virginia Polytechnic Institute and State University, Dec. 6, 2006, 105 pages.

Slupik, et al., "The stratigraphy of the Neogene-Quaternary succession in the southwest Netherlands from the Schelphoek borehole (42G4-11/42G0022)—a sequence-stratigraphic approach. Netherlands," Journal of Geosciences vol. 86, Issue 4, Dec. 2007, 16 pages.

Syvitski and Hutton, "2D SEDFLUX 1.0C: an advanced process-response numerical model for the fill of marine sedimentary basins," Computer and Geosciences vol. 27, Issue 6, Jul. 2001, 23 pages.

Syvitski and Hutton, "Failure of Marine Deposits and their Redistribution by Sediment Gravity Flows," Pure and Applied Geophysics, vol. 160, Issue 10-11, Oct. 2003, 17 pages.

Syvitski et al., "HydroTrend: a climate-driven hydrological transport model for predicting discharge and sediment to lakes or ocean," Computer Geoscience, vol. 24, Issue 1, Jan. 29, 1998, 18 pages.

Tetzlaff, "Input uncertainty and conditioning in siliciclastic process modelling, Geological Prior Information: Informing Science and Engineering," Geological Society, London, Special Publications, vol. 239, Jan. 2004, 15 pages.

Weltje et al., "Stratigraphic inversion of siliciclastic basin fills: a note on the distinction between supply signals resulting from tectonic and climatic forcing," Basin Research, vol. 10, Jun. 28, 1998, 25 pages.

Wijns et al, "Interactive inverse methodology applied to stratigraphic forward modelling," Geological Prior Information: Informing Science and Engineering, Geological Society, London, Special Publications vol. 239, 2004, 9 pages.

Wijns et al., "Inverse modelling in geology by interactive evolutionary computation," Journal of Structural Geology, vol. 25, Jan. 9, 2003, 11 pages.

Al-Bazzaz and Al-Mehanna, "Porosity, Permeability, MHR Calculations Using SEM and Thin-section Images for Characterizing Complex Mauddud-Burgan Carbonate Reservoir," Paper SPE-110730-MS presented at the Asia Pacific Oil and Gas Conference and Exhibition, Oct. 30-Nov. 1, 2007, 10 pages.

Asmussen et al., "Semi-automatic Segmentation of Petrographic This Section Images using a "Seeded-Region Growing Algorithm" with an Application to Characterize Wheathered Subarkose Sandstone," Computers & Geosciences, vol. 83, Issue C, Oct. 2015, 11 pages.

Barraud, "The use of watershed segmentation and GIS software for textural analysis of thin sections," Journal of Volcanology and Geothermal Research, vol. 154, Jun. 1, 2006, 17 pages.

Bartozzi et al., "Automated Grain Boundary Detection and Classification in Orientation Contrast Images," Journal of Structural Geology, Copyright 2000, pp. 1569-1579.

Bennetzen et al., "Automatic High-Throughput Detection of Fluid Inclusions in Thin-Section Images using a Novel Algorithm," Paper IPTC-17680 presented at the International Petroleum Technology Conference, Jan. 19-22, 2014, 11 pages.

Berrezueta et al. "Qualtitative and quantitative changes in detrital reservoir rocks caused by $CO_2$-brine—rock interactions during first injection phases (Utrillas sanstones, northern Spain)," Solid Earth vol. 7, Jan. 2016, 17 pages.

Blair and Berryman, "Estimation of Permeability and Relative Permeability for Sandstone using Image Analysis of Cross Sections" Rock Mechanics as a Multidisciplinary Science, Roegiers (ed.), Mar. 1991, 12 pages.

Buscombe, "Estimation of Grain-Size Distributions and Associated Parameters from Digital Images of Sediment," Sedimentary Geology, Copyright 2008, pp. 1-10.

Choh and Milliken, "Virtual Carbonate Thin Section using PDF: New Method for Interactive Visualization and Archiving," Carbonates and Evaporites, vol. 19, No. 2, Dec. 2004, 6 pages.

Choudhury et al., "Automated Grain Boundary Detection by CASRG," Journal of Structural Geology, Mar. 1, 2006, vol. 28, No. 3, pp. 363-375.

Das, "Morphology-Based Image Processing, In: Guide to Signals and Patterns in Image Processing: Foundations," Methods and Applications, Springer, Apr. 23, 2015, pp. 269-298, Abstract only, 3 pages.

DeVasto et al., "Using image Analysis and ARCGIS to Improve Automatic Grain Boundary Detection and Quantify Geological Images," Computers and Geosciences, vol. 49, Dec. 2012, 8 pages.

Francus, "An Image-Analysis Technique to Measure Grain-Size Variation in Thin Sections of Soft Clastic Sediments," Sedimentary Geology 121, Nov. 1998, 10 pages.

Fueten, "A Computer-Controlled Rotating Polarizer Stage for the Petrographic Microscope," Computers & Geosciences, vol. 23, No. 2, Mar. 1, 1997, pp. 203-208.

Goins and Reedy, "Digital Image Analysis in Microscopy for Objects and Architectural Conservation," Objects Specialty Group Postprints, vol. 7, Jun. 12, 2000, 16 pages.

Goodchild and Fueten, "Edge Detection in Petrographic Images Using the Rotating Polarizer Stage," Computers and Geosciences, vol. 24, No. 8, Oct. 1998, 7 pages.

Goodchild, "Geological Image Processing of Petrographic Thin Sections using the Rotating Polarizer Stage," A thesis submitted to the Department of Earth Sciences in partial fulfillment of the requirements for the degree of Master of Science, Brock University, St. Catharines, Ontario, Sep. 1998, 166 pages.

Graham et al., "Automated Sizing of Coarse-Grained Sediments: Image-Processing Procedures," Mathematical Geology, vol. 37, Issue 1, Jan. 2005, 28 pages.

Grove and Jerram, "jPOR: An ImageJ Macro to Quantify Total Optical Porosity From Blue-Stained Thin Sections," Computers & Geosciences, vol. 37, Nov. 2011, 10 pages.

Heilbronner, "Automatic Grain Boundary Detection and Grain Size Analysis Using Polarization Micrographs or Orientation Images," Journal of Structural Geology, Copyright 2000, pp. 969-981.

(56) References Cited

OTHER PUBLICATIONS

Hossain, "Relative Permeability Prediction from Image Analysis of Thin Sections," Paper SPE-143606, presented at the SPE EUROPEC/EAGE Annual Conference and Exhibition, May 23-26, 2011, 10 pages.

Iglesias et al., "Automatic recognition of hematite grains under polarized reflected light microscopy through image analysis," Minerals Engineering, Pergamon Press: Oxford, GB, vol. 24, No. 12, Apr. 12, 2011, pp. 1264-1270.

Izadi et al., "An intelligent system for mineral identificaiton in thin sections based on a cascade approach," Computers and Geoscience, vol. 99, Feb. 2017, 13 pages.

Kursun, "Particle Size and Shape Characteristics of Kemerburgaz Quartz Sands Obtained by Sieving, Laser Diffraction, and Digital Image Processing Methods," Mineral Processing and Extractive Metallurgy Review, vol. 30, Issue 4, Oct. 2009, 2 pages, Abstract only.

Layman, "Porosity Characterization Utilizing Petrographic Image Analysis: Implications for Identifying and Ranking Reservoir Flow Units, Happy Sprabeny Field, Garza County, Texas," Thesis Submitted to the Office of Graduate Studies of Texas A&M University in partial fulfillment of the requirements of the degree of Master of Science, May 2002, 114 pages.

Li et al., "GIS-based detection of grain boundaries," Journal of Structural Geology, Pergamon Press, vol. 30, No. 4, Dec. 27, 2007, pp. 431-443.

MacQueen, "Some Methods for classification and Analysis of Multivariate Observations," proceedings of 5th Berkeley Symposium on Mathematical Statistics and Probability, vol. 1, Jun. 21-Jul. 18, 1965, published by Berkeley, California, University of California Press, 1967, 17 pages.

Marschallinger and Hofmann, "The Application of Object Based Image Analysis to Petrographic Micrographs," Microscopy: Science, Technology, Applications and Education, A. Mendez-Vilas and J. Diaz (Eds.), FORMATEX, Dec. 2010, 7 pages.

Obara et al., "Utilisation of the Image Analysis Method for the Detection of the Morphological Anisotropy of Calcite Grains in Marble," Computer Geoscience, Copyright 2007, 7 pages.

Obara, "An Image Processing Algorithm for the Reversed Transformation of Rotated Microscope Images," Computers & Geosciences, Copyright 2007, pp. 853-859.

Perring et al., "Using Automated Digital Image Analysis to Provide Quantitative Petrographic Data on Olivine-Phyric Basalts," Computers & Geosciences, vol. 30, Mar. 2004, 13 pages.

Reedy and Kamboj, "Image Analysis Protocol Instructions #1: Spatial Calibration of Images, Project Report," University of Delaware, Laboratory of Analysis of Cultural Materials, 2004, 9 pages.

Reedy et al., "Image Analysis in Quantitative Particle Studies of Archaeological Ceramic Thin Sections," Advances in Archaeological Practice, vol. 2, No. 4, Nov. 2014, 17 pages.

Reedy, "Review of Digital Image Analysis of Petrographic Thin Sections in Conservation Research," Journal of the American institute for Conservation, vol. 45, Issue 2, Jun. 2006, 8 pages.

Richa et al., "Image Analysis and Pattern Recognition for Porosity Estimation from Thin Sections," SEG Technical Program Expanded Abstracts, Jan. 2006, 5 pages.

Rostami et al., "Developing a Committee Machine Model for Predicting Reservoir Porosity from Image Analysis of Thin Sections," proceedings of the 20th Formation Evaluation Symposium of Japan, Oct. 1-2, 2014, 11 pages.

Ruzyla, "Characterization of Pore Space by Quantitative Image Analysis," SPE Formation Evaluation, Aug. 1986, 10 pages.

Sharma and Sharma, "Image Segmentation Using Morphological Operation for Automatic Region Growing," International Journal of Innovative Research in Computer and Communication Engineering, vol. 2, Issue 9, Sep. 2014, 7 pages.

Smith and Beermann, "Image Analysis of Plagioclase Crystals in Rock Thin Sections using Grey Level Homogeneity Recognition of Discrete Areas," Computers & Geosciences 33, Mar. 2007, 22 pages.

Starkey et al., "A Microcomputer-Based System for Quantitative Petrographic Analysis," Computers & Geosciences, vol. 20, No. 9, Copyright 1994, pp. 1285-1296.

Št'astná et al., "Cathodoluminescence Microscopy and Petrographic Image Analysis of Aggregates in Concrete Pavements Affected by Alkali-Silica Reaction," Materials Characterization, vol. 65, Mar. 2012, 11 pages.

Tarquini et al., "A Microscopic Information System (MIS) for Petrographic Analysis," Computers and Geosciences, vol. 36, No. 5, May 1, 2010, pp. 665-674.

Wardaya et al., "Integrating Digital Image Processing and Artificial Neural Network for Estimating Porosity from Thin Section," Paper IPTC-16959, presented at the International Petroleum Technology Conference, Mar. 26-28, 2013, 10 pages.

Zhou et al., "Segmentation of Petrographic Images by Integrating Edge Detection and Region Growing," Computers & Geosciences, Copyright 2004, pp. 817-831.

Duan et al, "Similarity measure of sedimentary successions and its application in inverse stratigraphic modeling", Petroleum Science, China University of Petroleum (Beijing), Heidelberg, vol. 14, No. 3, Jul. 24, 2017 (Jul. 24, 2017), pp. 484-492. 9 pages.

Hussain et al, "Moving Models into Reality: An Automated Workflow to Calibrate Forward Strati graphic Modeling; Application to Hani fa and Arab-D in Central Saudi Arabia", SPE-188920-MS, Abu Dhabi International Petroleum Exhibition & Conference, Jan. 1, 2017. 11 pages.

International Search Report and Written Opinion issued in International Application No. PCT/US2019/032489 dated Aug. 19, 2019, 17 pages.

GCC Examination Report in GCC Appln. No. GC 2019-37381, dated May 22, 2020, 4 pages.

GCC Examination Report in GCC Appln. No. GC 2019-37381, dated Oct. 26, 2020, 4 pages.

Rijks et al., "Attribute extraction: an important application in any detailed 3-D interpretation study," Geophysics: The Leading Edge of Exploration, Sep. 1991, 9 pages.

\* cited by examiner

AUTOMATED ANALYSIS OF PETROGRAPHIC THIN SECTION IMAGES USING ADVANCED MACHINE LEARNING TECHNIQUES

BACKGROUND

This specification relates to methods for analyzing petrographic thin section images.

A common issue in geological petrography work is the analysis of thin sections. Thin section analysis may be used to determine properties of the thin section such as mineral composition and texture.

Hydrocarbon fluids may be found in the pore spaces visible in thin sections. The study of geological thin sections has become one of the most important disciplines for hydrocarbon exploration.

Conventionally, thin section analysis has been performed by a point counting method. Point counting in thin sections is normally conducted through mechanical or electromechanical devices attached to a microscope. Such mechanical and electromechanical devices can be very expensive and offer limited functionality. The final results of point counting analysis are subjective and dependent on expertise of the user who performed the point counting.

SUMMARY

This specification describes a system implemented as computer programs on one or more computers in one or more locations that performs automated analysis of petrographic thin section images.

According to a first aspect there is provided a method for automated analysis of petrographic thin section images. The method includes determining a first image of a petrographic thin section of a rock sample, for example, by a polarizing microscope. A feature vector is determined for each pixel of the first image, where the feature vector of each respective pixel is determined based at least on the color (for example, luminosity and chromaticity) exhibited by the respective pixel. Multiple different regions of the petrographic thin section are determined by clustering (for example, by a k-means algorithm) the pixels of the first image based on the feature vectors of the pixels of the first image. One of the regions corresponds to grains in the petrographic thin section, and other regions may correspond to, for example, pores, clays, or iron oxides in the petrographic thin section.

A second image of the petrographic thin section is determined by combining images of the petrographic thin section acquired with plane-polarized light and cross-polarized light. Grains are segmented from the second image of the petrographic thin section using a segmentation method (for example, a watershed segmentation method). The segmentation is enhanced by incorporating the regions determined from the first image, including the region corresponding to grains in the thin section. Characteristics of the segmented grains are determined based on the grain segmentation.

In some implementations, relative proportions of the multiple different regions of the petrographic thin section are determined.

In some implementations, the characteristics of the segmented grains include, for each of the grains, at least one of: area, perimeter, long axis diameter, short axis diameter, or roundness.

In some implementations, the first image is an image of the petrographic thin section acquired (for example, by a polarizing microscope) with plane-polarized light.

In some implementations, each image acquired with cross-polarized light (for example, that is used to determine the second image) is acquired when the petrographic thin section is rotated to a different angle relative to a reference angle. Each of these images may subsequently be registered to a reference image.

In some implementations, the determined regions of the thin section and the characteristics of the segmented grains are used to evaluate a quality of a reservoir.

According to a second aspect there is provided a system that performs the operations of the previously described method. The system includes a data processing apparatus and a non-transitory computer readable storage medium in data communication with the data processing apparatus. The non-transitory storage medium stores instructions executable by the data processing apparatus. When the data processing apparatus executes the instructions stored by the non-transitory storage medium, the data processing apparatus is caused to perform the operations of the previously described method.

According to a third aspect, there is provided a non-transitory computer readable storage medium. The non-transitory storage medium stores instructions executable by a data processing apparatus. Upon execution of the instructions, the data processing apparatus is caused to perform the operations of the previously described method.

Particular embodiments of the subject matter described in this specification can be implemented so as to realize one or more of the following advantages.

The thin section analysis system as described in this specification uses advanced machine learning and automated image processing methods to process thin section images and achieves several advantages over manual systems for thin section image analysis. First, the thin section analysis system as described in this specification can be implemented to perform thin section image analysis orders of magnitude faster than manual methods for thin section image analysis (such as point counting methods). For example, the thin section analysis system as described in this specification can be implemented to process thin section images in two minutes or less, whereas conventional point counting methods (that require a geologist to manually examine the thin section images at a large number of different points) may take up to four hours. Second, the thin section analysis system as described in this specification may be more accurate than manual methods for thin section image analysis. For example, the thin section analysis system as described in this specification relies on machine learning and automated image analysis algorithms and thereby obviates sources of human error that are present in manual methods for thin section image analysis. For example, point counting methods for thin section image analysis place a high cognitive burden on the user performing the point counting method, increasing the likelihood of human errors such as the user incorrectly counting the number of grains or pores in a region of a thin section image. Third, the thin section analysis system as described in this specification is consistent and eliminates potential biases present in manual methods for thin section image analysis. For example, a user that performs a point counting method multiple times on a single thin section image to determine an estimate of a characteristic of a thin section image (for example, the average diameter of grains in the thin section) may determine different values each time. In contrast, the thin section analysis system as described in this specification will determine consistent estimates of the same characteristic.

The thin section analysis system as described in this specification performs a comprehensive analysis of the thin section characteristics, including both the compositional properties of the thin section (for example, the fraction of the thin section occupied by pores) and properties of the grains of the thin section (for example, the distribution of grain diameters in the thin section). In contrast, many conventional thin section analysis systems perform a less comprehensive analysis by identifying fewer relevant properties of thin sections.

The thin section analysis system as described in this specification is fully automated and thereby enables more efficient use of computational resources than conventional systems that are not fully automated. Conventional systems that are not fully automated require user intervention (for example, to manually calibrate system parameters). User intervention can be time consuming (potentially ranging from seconds to hours), and during user intervention the computational resources of such conventional systems (for example, processing power) are not utilized. Since the thin section analysis system as described in this specification is fully automated it can operate continuously and thereby utilize computational resources more efficiently.

The details of one or more embodiments of the subject matter of this specification are set forth in the accompanying drawings and the description. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
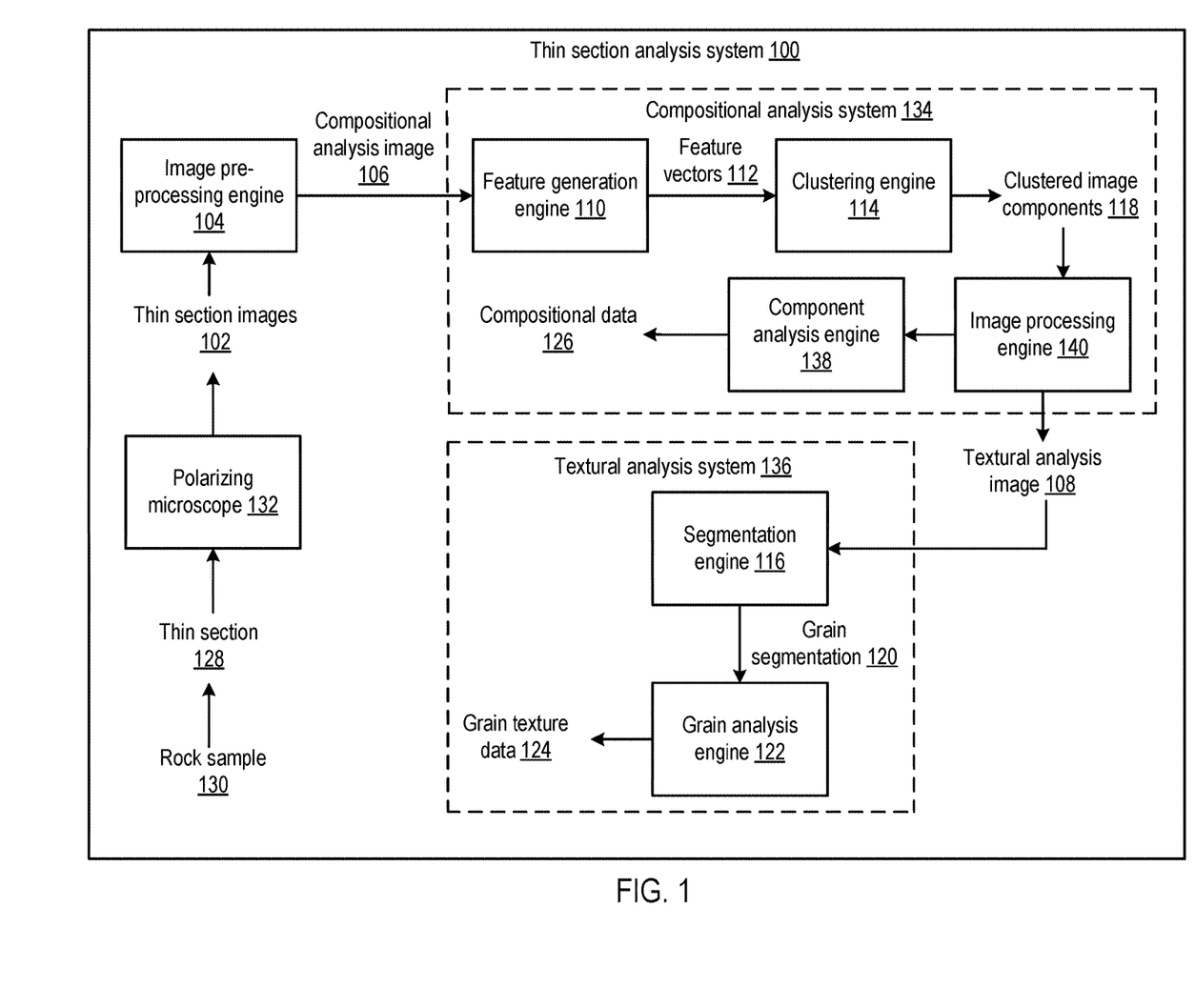
FIG. 1 is an illustration of an example thin section analysis system.

FIG. 1 shows an example thin section analysis system 100. The thin section analysis system 100 is an example of a system implemented as computer programs on one or more computers in one or more locations in which the systems, components, and techniques described later are implemented.

The thin section analysis system 100 processes thin section images 102 of a thin section 128 from a rock sample 130 using a compositional analysis system 134 and a textural analysis system 136 to generate as output data characterizing properties of the thin section 128. The compositional analysis system 134 generates compositional data 126 that indicates the relative proportions of the thin section 102 that are occupied by each of multiple thin section components, such as: grains, pores, clays, and iron oxides. The textural analysis system 136 generates grain texture data 124 including data characterizing one or more of the areas, the perimeters, the long axis diameters, the short axis diameters, or the roundness of the grains in the thin section 128.

Rock samples 130 may be obtained from outcrops, cores, cuttings, or from any other source of rock samples.

The thin section 128 of the rock sample 130 is generated by securing the rock sample 130 to a glass slide (using any appropriate thin section generation process).

In some cases, when the rock sample 130 is obtained in the vicinity of a petroleum reservoir, the compositional data 126 and the grain texture data 124 generated by the system 100 can be used to evaluate reservoir quality, plan reservoir stimulation procedures, assess the potential for formation damage to the reservoir, or reconstruct the diagenetic and geochemical history of the reservoir.

For example, the compositional data 126 indicates the relative proportions of the thin section 102 that are occupied by grains and pores, and thereby characterizes the porosity and compaction of the rock sample 130, which are indicators of reservoir quality. As another example, the compositional data 126 indicates the relative proportion of the thin section 102, and by extension the rock sample 130, that is occupied by clay. The volume of clay in a rock sample 130 is an indicator of reservoir quality, since clay occupies pore spaces that could otherwise be occupied by petroleum. As another example, the grain texture data 124 can indicate the diameters of the grains in the thin section 128, and by extension the rock sample 130, and thereby indicate the permeability of the rock sample 130, which is an important factor affecting reservoir quality. Specifically, larger grain sizes may indicate higher rock permeability and thereby suggest higher reservoir quality.

Multiple thin section images 102 of the thin section 128 are generated by a polarizing microscope 132. The polarizing microscope 132 is configured to generate the thin section images 102 by acquiring magnified images of the thin section 128 while exposing the thin section 128 to linearly-polarized light (that is, light where the magnetic or electric field vector are confined to a plane along the direction of propagation). The thin section images 102 include images of the thin section 128 acquired when the polarizing microscope 132 exposes the thin section 128 to linearly-polarized light and images of the thin section 128 acquired when the polarizing microscope 132 exposes the thin section 128 to cross-polarized light. Different thin section images 102 are acquired by rotating the position of the thin section 128 in the polarizing microscope to different angles relative to a reference angle and acquiring images of the thin section 128 while it is rotated to the different angles. The different angles may include the angles 0°, 22.5°, 45°, 67.5°, or any other appropriate angles. The thin section images 102 are color images, that is, images that include color data from different color channels for each image pixel. For example, the thin section images 102 may be red-green-blue ("RGB") images, that is, images that include color data for a red color channel, a green color channel, and a blue color channel for each image pixel. As another example, the thin section images 102 may be images that include color data for a luminosity channel and a chromaticity channel.

The system 100 includes an image pre-processing engine 104 that is configured to process the thin section images 102 to convert them to a luminosity-chromaticity format (if necessary) using any appropriate color-space conversion technique. A color-space conversion technique refers to a mathematical transformation that is applied to the pixels of an image represented in accordance with one color format to represent them in accordance with another color format. Examples of color formats include the grayscale color format, the RGB color format, and the luminosity-chromaticity format.

The system 100 provides a compositional analysis image 106 to the compositional analysis system 134. In general, the compositional analysis image 106 can be any pre-processed (that is, by the image pre-processing engine 104) thin section image or combination of thin section images. For example, the compositional analysis image 106 may be a thin section image that is acquired with plane-polarized light.

The compositional analysis system 134 processes the compositional analysis image 106 to generate as output compositional data 126. The compositional data 126 indicates the relative proportions of the thin section 102 that are occupied by respective thin section components such as grains, pores, clays, and iron oxides. In some cases, the compositional data 126 additionally indicates the relative proportions of the thin section 102 that are occupied by additional components, such as cement. In general, the description that follows can be applied analogously to determine compositional data for any number of different thin section components.

The compositional analysis system 134 provides the compositional analysis image 106 as input to a feature generation engine 110 that is configured to determine a feature vector 112 (that is, an ordered collection of numerical values) for each respective pixel of the compositional analysis image 106 based on at least the color components of each respective pixel, as will be described in more detail later.

The compositional analysis system 134 provides the feature vectors 112 for the respective pixels of the compositional analysis image 106 as input to a clustering engine 114 that is configured to cluster the pixels of the compositional analysis image 106 (using a machine learning clustering algorithm) based on the feature vectors 112 of the pixels of the compositional analysis image 106. The clustering engine 114 generates clustered image components 118 that indicate, for each respective pixel of the compositional analysis image 106, that the pixel corresponds to a particular thin section component.

The compositional analysis system 134 provides the clustered image components 118 as input to an image processing engine 140. The image processing engine 140 processes the clustered image components 118 to: (i) convert them to a storage format that can be processed by a component analysis engine 138, and (ii) generate a textural analysis image 108 (to be provided as input to the textural analysis system 136). In general, the image processing engine 140 generates the textural analysis image 108 by combining: (i) one or more of the pre-processed thin section images 102, and (ii) a mask image based on the clustered image components 118. An example process for determining a thin section textural analysis image is described with reference to FIG. 4.

The component analysis engine 138 is configured to process the representation of the clustered image components 118 output by the image processing engine 140 to determine the compositional data 126. To determine the relative proportion of the thin section 128 that is occupied by a particular component (for example, grains, pores, clays, or iron oxides), the component analysis engine 138 determines the fraction of pixels of compositional analysis image 106 that correspond to the particular component based on the clustered image components.

An example process for determining compositional data for a thin section is described with reference to FIG. 2.

The textural analysis system 136 processes the textural analysis image 108 (generated by the image processing engine 140) to generate as output grain texture data 124. The grain texture data 124 includes data characterizing one or more of the areas, the perimeters, the long axis diameters, the short axis diameters, or the roundness of the grains in the thin section 128.

The textural analysis system 136 provides the textural analysis image 108 as input to a segmentation engine 116 that is configured to process the input to generate as output a grain segmentation 120. The grain segmentation 120 includes data indexing the grains of the thin section 128 (that is, data that associates each grain of the thin section 128 to a different numerical index value) and indicates, for each respective pixel of the textural analysis image 108, either that the pixel does not correspond to a grain or that the pixel corresponds to a particular grain of the thin section 128.

The textural analysis system 136 provides the grain segmentation 120 as input to a grain analysis engine 122 that is configured to process the input to generate as output the grain texture data 124. To determine the properties of the grains of the thin section 102 (for example, the areas, the perimeters, the long axis diameters, the short axis diameters, or the roundness of the grains), the grain analysis engine 122 individually processes each of the grains of the thin section 128 indexed by the grain segmentation 120 and determines the corresponding properties of the grain.

An example process for determining grain texture data for a thin section is described with reference to FIG. 3.

Figure 2:
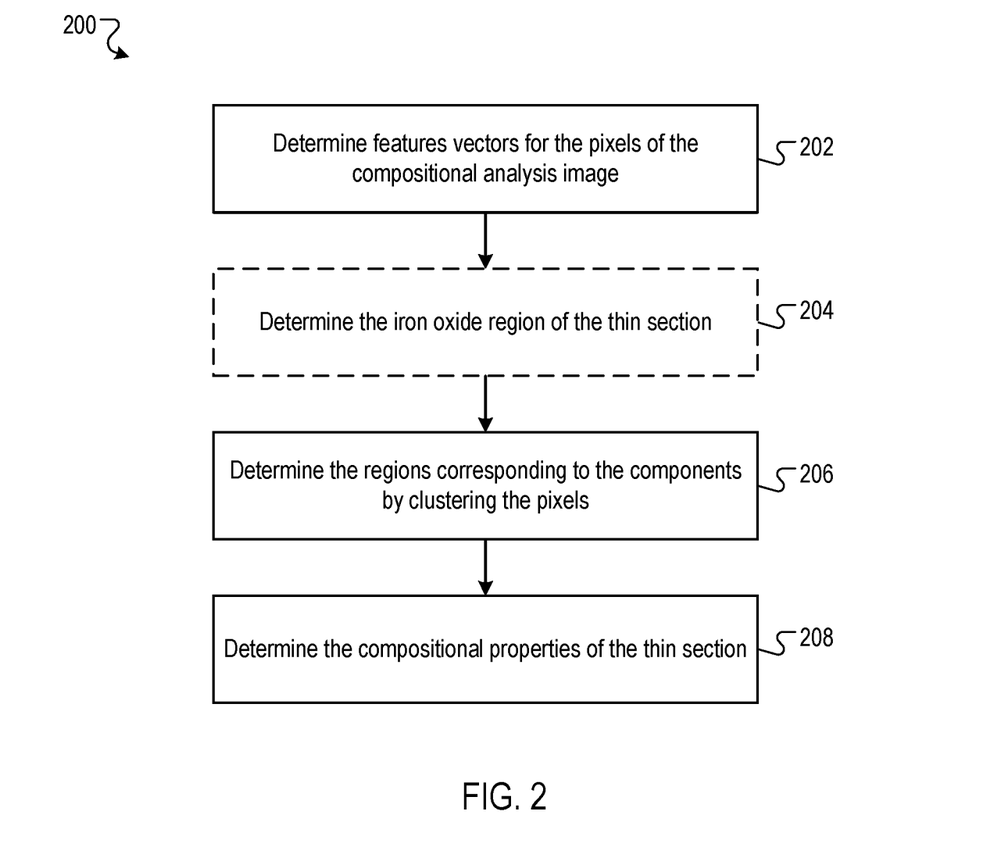
FIG. 2 is a flow diagram of an example process for determining compositional data for a thin section.

FIG. 2 is a flow diagram of an example process for determining compositional data for a thin section. For convenience, the process 200 will be described as being performed by a system of one or more computers located in one or more locations. For example, a compositional analysis system, for example, the compositional analysis system 134 of FIG. 1, appropriately programmed in accordance with this specification, can perform the process 200.

The system determines a feature vector for each respective pixel of the compositional analysis image (202). In general, the feature vector for each respective pixel of the compositional analysis image includes the color components corresponding to the respective pixel. For example, if the compositional analysis image is a luminosity-chromaticity image, then the feature vector for a respective pixel includes the values of the luminosity and chromaticity channels of the respective pixel. In some implementations, the feature vector for each respective pixel of the compositional analysis image includes other features derived from the neighborhood of the respective pixel in the compositional analysis image, such as mean color intensities and variances of color intensities in neighborhoods of the respective pixel.

In some implementations, the system determines the region of the compositional analysis image corresponding to the iron oxides component by determining which pixels of the compositional analysis image have a feature vector that is sufficiently similar to a reference feature vector known to correspond to iron oxides (204). For example, for certain compositional analysis images, iron oxides have a black color, while other components of the thin section (for example, pores, grains, and clays) do not have a black color. In this example, the system may determine that pixels with color features that are sufficiently similar to a black color correspond to iron oxides. In some other implementations, the system does not perform 204, and rather determines the regions of the compositional analysis image corresponding to each different thin section component (including the region corresponding to iron oxides) by clustering the pixels, as described with reference to 206.

The system determines the regions of the compositional analysis image corresponding to the respective thin section components (such as grains, pores, clays, and in some cases, iron oxides) by clustering the pixels of the compositional analysis image based on their feature vectors (206). An example process for determining thin section regions by clustering is described with reference to FIG. 5.

The system determines the compositional properties of the thin section based on the determined regions (that is, the regions corresponding to each different thin section component) (208). The compositional properties of the thin section include the relative proportions of the thin section that are occupied by the different thin section components. Specifically, to determine the proportion of the thin section that is occupied by a component c, the system computes:

$$\frac{\text{number of pixels in region } c}{\text{total number of pixels}} \times 100\%,$$

where the component c may correspond to grains, pores, clays, iron oxides, or any other relevant component.

In some implementations, the system may compute other compositional properties of the thin section, such as the absolute area (for example, in square millimeters) of each region of the thin section corresponding to each respective component.

Figure 3:
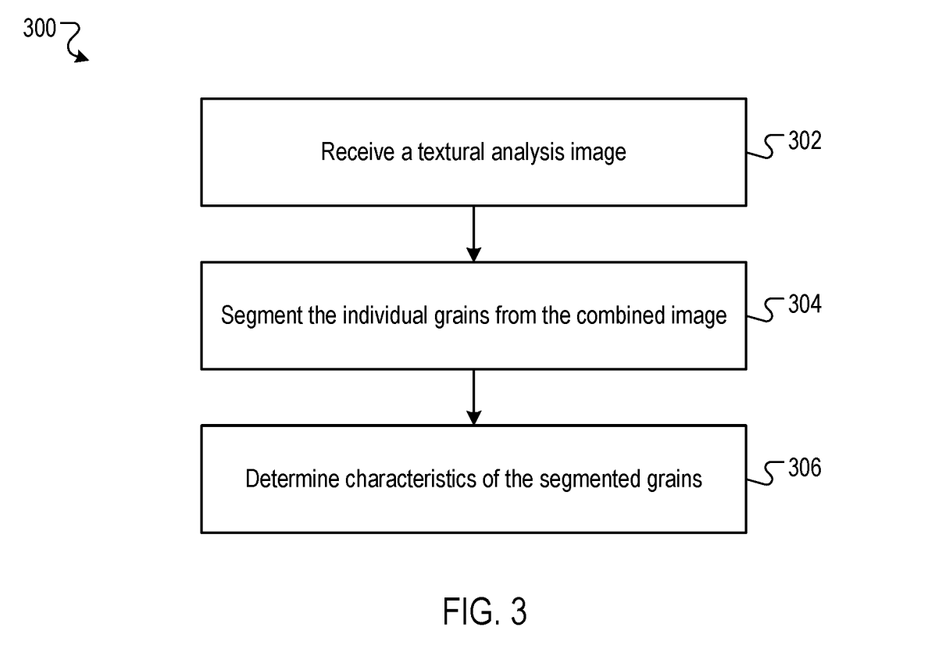
FIG. 3 is a flow diagram of an example process for determining grain texture data for a thin section.

FIG. 3 is a flow diagram of an example process for determining grain texture data for a thin section. For convenience, the process 300 will be described as being performed by a system of one or more computers located in one or more locations. For example, a textural analysis system, for example, the textural analysis system 136 of FIG. 1, appropriately programmed in accordance with this specification, can perform the process 300.

The system receives a textural analysis image (302). In general, the textural analysis is generated by combining one or more thin section images with a mask image of one or more thin section components. An example process for determining a thin section textural analysis image is described with reference to FIG. 4.

The system segments the individual grains from the textural analysis image (304). Segmenting the grains from the textural analysis image includes generating data indexing the grains of the thin section (that is, data that associates each grain of the thin section to a different numerical index value) and data that indicates, for each respective pixel of the textural analysis image, either that the pixel does not correspond to a grain (that is, the pixel is a background pixel) or that the pixel corresponds to a particular grain of the thin section (that is, a grain indexed by a particular index value).

The system can segment the grains using any appropriate segmentation algorithm. In general, the segmentation algorithm is an algorithm that is mainly automated (that is, an algorithm that requires little to no human intervention). For example, the system may segment the grains from the textural analysis image using an image processing method, such as a watershed segmentation algorithm. In this example, the system processes the textural analysis image to generate an edge image, where the intensity of a pixel is correlated to the likelihood that the pixel belongs to an edge of the textural analysis image. The edge image delineates the grains of the thin section, and a watershed segmentation algorithm is applied to the edge image to segment the grains. Generally, a watershed segmentation algorithms determines a segmentation of an image into different regions by determining regions of the image that are enclosed by boundaries characterized by high pixel intensities (for example, by a flooding algorithm). By way of other examples, the system may segment the grains from the textural analysis image using machine learning segmentation methods, such as random forest or neural network segmentation methods.

The system determines the characteristics of the segmented grains (306). The characteristics of the segmented grains include one or more of the areas, the perimeters, the long axis diameters, the short axis diameters, and the roundness of the grains. The system individually processes each of the segmented grains and determines the corresponding properties of the grain. For example, the system can determine the area of a segmented grain by multiplying the number of pixels in the segmented grain by the area occupied by a single pixel.

In some implementations, the system determines aggregate characteristics of the segmented grains. For example, the system may determine the distribution of the areas of the segmented grains, the average area of the segmented grains, or the variance in the areas of the segmented grains.

Figure 4:
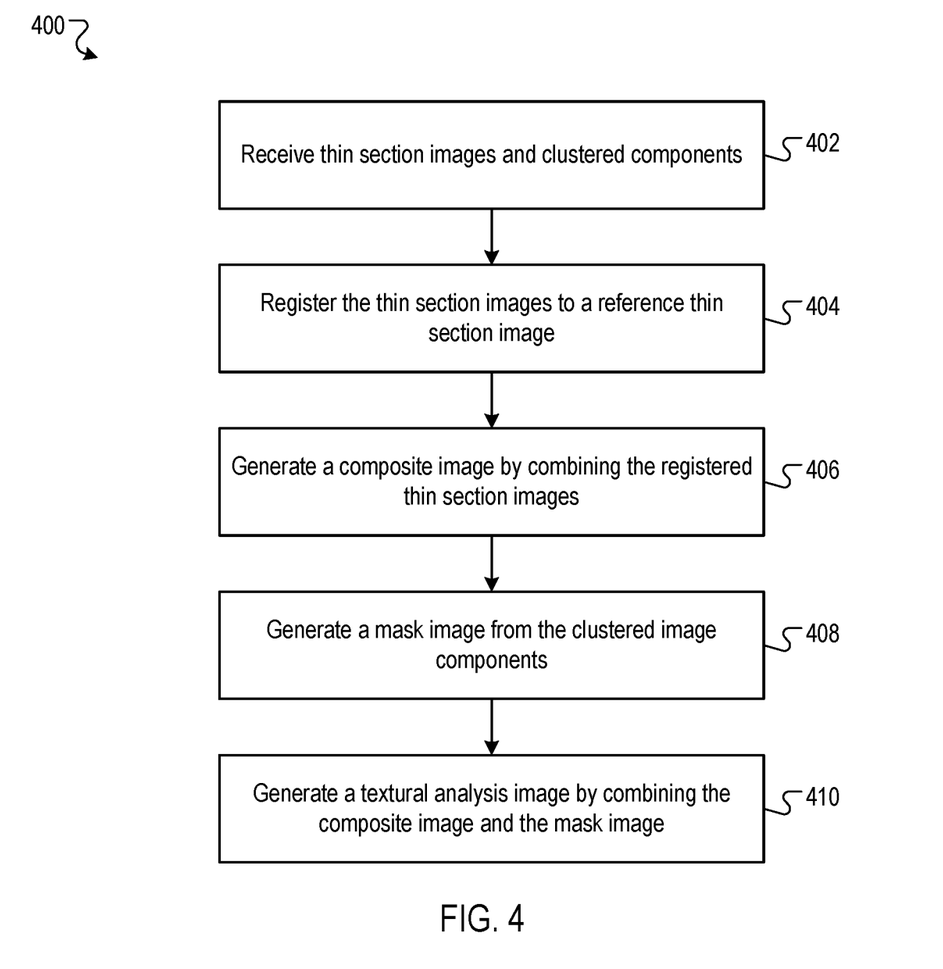
FIG. 4 is a flow diagram of an example process for determining a thin section textural analysis image.

FIG. 4 is a flow diagram of an example process for determining a thin section textural analysis image. For convenience, the process 400 will be described as being performed by a system of one or more computers located in one or more locations. For example, a thin section analysis system, for example, the thin section analysis system 100 of FIG. 1, appropriately programmed in accordance with this specification, can perform the process 400.

The system receives multiple images of the thin section generated by a polarizing microscope and clustered image components (indicating the regions of the thin section corresponding to the different thin section components) (402).

The polarizing microscope is configured to generate the thin section images by acquiring magnified images of the thin section while exposing the thin section to linearly-polarized light (that is, light where the magnetic or electric field vector are confined to a plane along the direction of propagation). The thin section images include images of the thin section acquired when the polarizing microscope exposes the thin section to linearly-polarized light and images of the thin section acquired when the polarizing microscope exposes the thin section to cross-polarized light. Different thin section images are acquired by rotating the position of the thin section in the polarizing microscope to different angles in the polarizing microscope relative to a reference angle and acquiring images of the thin section while it is rotated to the different angles. The different angles may include the angles 0°, 22.5°, 45°, 67.5°, or any other appropriate angles. The thin section images are color images, that is, images that include color data from different color channels for each image pixel. For example, the thin section images may be RGB images, that is, images that include color data for a red color channel, a green color channel, and a blue color channel for each image pixel. As another example, the thin section images may be images that include color data for a luminosity channel and a chromaticity channel.

The system registers the multiple thin section images to a reference thin section image (404). In general, the reference thin section image can be any thin section image. In some cases, the reference thin section image is the compositional analysis image. The system can use any appropriate registration algorithm. The registration algorithm can employ a linear registration transformation, an elastic registration transformation, or any other appropriate registration transformation. The registration algorithm can include a sum of squared differences objective function, a mutual information objective function, or any other appropriate objective function.

Each of the multiple thin section images may have been acquired while rotated to a different angle in the polarizing microscope. In some implementations, the system de-rotates each of the multiple thin section images relative to the reference thin section image prior to registering them to the reference thin section image. The system de-rotates a thin section image relative to the reference thin section image by determining the difference between the acquisition angle of the thin section image and the reference thin section image, and digitally rotating the thin section by the opposite of the determined angle. For example, if the system determines that the difference between the acquisition angle of the thin section image and the reference thin section image is 35° clockwise, then the system rotates the thin section image 35° counter-clockwise.

The system combines the registered thin section images to generate a composite image (406). In some cases, prior to combining the registered thin section images, the system converts them to corresponding grayscale images. In some implementations, the system combines the registered thin section images by averaging them (that is, by setting the value of each pixel of the combined image to be the average of the values of the corresponding pixels of the registered thin section images). In some implementations, the system combines the registered thin images by computing their median (that is, by setting the value of each pixel of the combined image to be the median of the values of the corresponding pixels of the registered thin section images).

The system generates a mask image from the clustered image components (408). Specifically, the system generates a mask image of the grain component of the thin section, the pore component of the thin section, or both. A mask image of one or more components of a thin section refers to an image where pixels belonging to the one or more components have a first predetermined value (for example, the value of one) and pixels that do not belong to the one or more components have a second predetermined value (for example, the value of zero).

The system combines the composite image and the mask image to generate a textural analysis image (410). The composite image and the mask image may be combined in any appropriate manner. For example, the composite image and the mask image may be combined by setting the value of each pixel of the textural analysis image to be the product of the values of the corresponding pixels of the composite image and the mask image, thereby highlighting the grain region in the textural analysis image.

Figure 5:
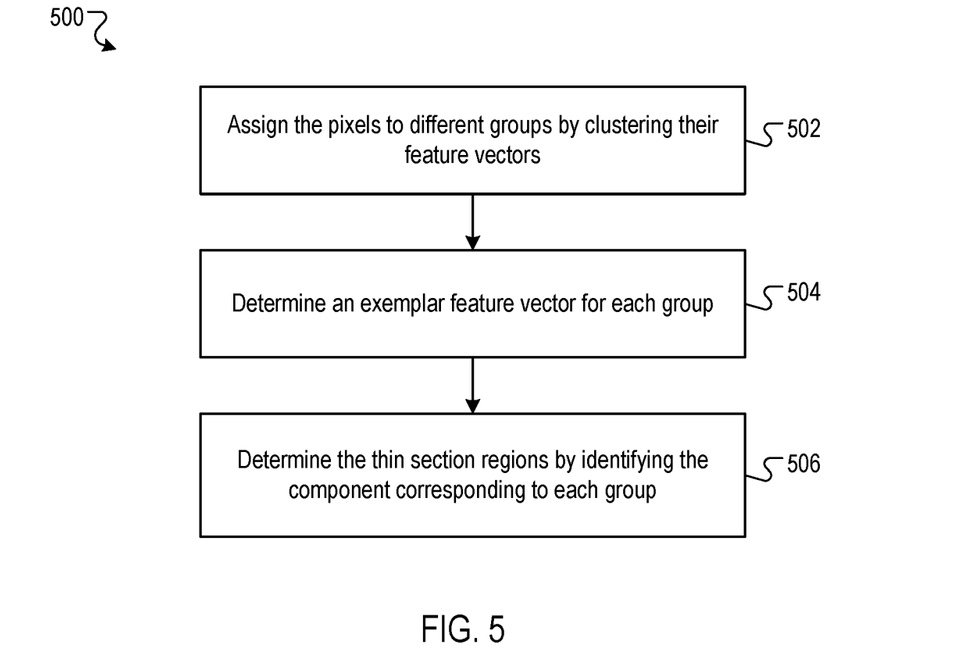
FIG. 5 is a flow diagram of an example process for determining thin section regions by clustering.

FIG. 5 is a flow diagram of an example process for determining thin section regions by clustering. Specifically, FIG. 5 describes an example process for determining thin section regions by clustering feature vectors of pixels of an image of the thin section (for example, the compositional analysis image 106). For convenience, the process 500 will be described as being performed by a system of one or more computers located in one or more locations. For example, a compositional analysis system, for example, the compositional analysis system 134 of FIG. 1, appropriately programmed in accordance with this specification, can perform the process 500.

The system assigns the pixels of the image of the thin section to different groups by clustering their feature vectors (502). The feature vector of a pixel refers to an ordered collection of numerical values associated with the pixel. Clustering the pixels of an image based on their feature vectors refers to assigning each of the pixels of the image to one of a predetermined number of different groups. The assignment is performed to minimize the differences between the feature vectors of pixels within groups and to maximize the differences between the features vectors of pixels between different groups. The system can use any appropriate clustering algorithm to cluster the pixels based on their feature vectors. For example, the system can use a k-means clustering algorithm, an expectation-maximization clustering algorithm, or a clustering algorithm based on neural networks.

In some cases, the clustering algorithm is run for a predetermined number of iterations. In some cases, the clustering algorithm is run until the clusters predicted by the clustering algorithm have converged. For example, the clustering algorithm may be determined to have converged if the difference in the assignments of pixels to clusters between iterations is less than a predetermined threshold.

The system selects the number of predetermined groups in the clustering algorithm based on the number of clustered image components to be determined—for example, if the clustered image components to be determined correspond to pores, grains, and clays, the system selects the number of predetermined groups to be three.

The system determines a respective exemplar feature vector for each group of the predetermined number of groups (504). For example, the exemplar feature vector for a group may be determined as the average of the feature vectors of the pixels assigned to the group. As another example, the exemplar feature vector for a group may be determined as the centroid of the feature vectors of the pixels assigned to the group.

The system determines the clustered image components by identifying the thin section component (for example, pores, grains, or clays) corresponding to each group (506). Specifically, the system compares the exemplar feature vectors for each group to reference feature vectors for each component. A different reference feature vector corresponds to each component. For example, if the components are pores, grains, and clays, then a first reference feature vector would correspond to pores, a second reference feature vector would correspond to grains, and a third reference feature vector would correspond to clays. The reference feature vector for a component is a feature vector that is known (for example, from previous experiments) to be approximately representative of the feature vectors of pixels corresponding to the component. The system determines that the pixels in a given group (as determined by the clustering) correspond to a particular component if the exemplar feature vector of the group is sufficiently similar to the reference feature vector of the particular component. The system may determine that an exemplar feature vector is sufficiently similar to a reference feature vector if the distance between the exemplar feature vector and the reference feature vector (for example, as determined by the Euclidean distance measure) is less than a predetermined threshold.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, that is, one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, for example, a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, for example, an FPGA (field programmable gate array) or an ASIC (application-specific integrated circuit). The apparatus can optionally include, in addition to hardware, code that creates an execution environment for computer programs, for example, code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language (for example, compiled or interpreted languages, or declarative or procedural languages). A computer program can be deployed in any form, including as a stand-alone program or as a module, component, subroutine, or other unit suitable for use in a computing environment. A program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, for example, an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include (or be operatively coupled to share data with) one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device, for example, a universal serial bus (USB) flash drive, to name just a few.

Computer-readable media suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks.

To provide for interaction with a user, embodiments of the subject matter described in this specification can be implemented on a computer having a display device, for example, a CRT (cathode ray tube) or LCD (liquid crystal display) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, for example, a smartphone that is running a messaging application, and receiving responsive messages from the user in return.

Data processing apparatus for implementing machine learning models can also include, for example, special-purpose hardware accelerator units for processing common and compute-intensive parts of machine learning training or production (for example, inference) workloads.

Machine learning models can be implemented and deployed using a machine learning framework, for example, a TensorFlow framework, a Microsoft Cognitive Toolkit framework, an Apache Singa framework, or an Apache MXNet framework.

Embodiments of the subject matter described in this specification can be implemented in a computing system that includes a back-end component, for example, as a data server, or that includes a middleware component, for example, an application server, or that includes a front-end component, for example, a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, for example, a communication network. Examples of communication networks include a local area network (LAN) and a wide area network (WAN), for example, the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, for example, a hypertext markup language ("HTML") page, to a user device, for example, for purposes of displaying data to and receiving user input from a user interacting with the device, which acts as a client. Data generated at the user device, for example, a result of the user interaction, can be received at the server from the device.

While this specification contains many specific implementation details, these should not be construed as limitations on the scope of the description in the specification or on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described earlier as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described earlier should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A method for automated analysis of petrographic thin section images, the method comprising:
   determining a first image of a petrographic thin section of a rock sample;
   determining a feature vector for each pixel of the first image, wherein the feature vector of each respective pixel is determined based at least on color characteristics of the respective pixel;
   determining multiple different regions of the petrographic thin section by clustering the pixels of the first image based on the feature vectors of the pixels of the first image over a plurality of clustering iterations using an iterative clustering technique, wherein one of the regions is a grain region that corresponds to grains in the petrographic thin section; and
   determining a second image of the petrographic thin section, comprising:
      combining images of the petrographic thin section acquired with plane-polarized light and cross-polarized light;
      segmenting multiple grains from the second image of the petrographic thin section based on the multiple different regions from the first image, comprising:
         generating a mask image based on the multiple different regions from the first image, wherein: (i) pixels of the mask image that are included in the grain region have a first predetermined value, and (ii) pixels of the mask image that are not included in the grain region have a second, different predetermined value;
         highlighting the grain region in the second image by applying the mask image to the second image; and
         after applying the mask image to the second image, segmenting multiple grains from the second image using a segmentation algorithm; and
      determining characteristics of the segmented grains.

2. The method of claim 1, wherein the multiple different regions of the petrographic thin section correspond to at least one of grains, pores, clays, or iron oxides.

3. The method of claim 2, further comprising determining relative proportions of the multiple different regions of the petrographic thin section.

4. The method of claim 1, wherein the characteristics of the segmented grains include, for each of the multiple grains, at least one of area, perimeter, long axis diameter, short axis diameter, or roundness.

5. The method of claim 1, wherein clustering the pixels of the first image comprises applying a k-means clustering algorithm to the pixels of the first image.

6. The method of claim 1, wherein the multiple grains are segmented using a watershed segmentation algorithm.

7. The method of claim 1, wherein the first image is an image of the petrographic thin section acquired with plane-polarized light.

8. The method of claim 1, wherein each image acquired with cross-polarized light is acquired when the petrographic thin section is rotated to a different angle relative to a reference angle, and determining a second image of the petrographic thin section further comprises registering the multiple acquired images to a reference image.

9. The method of claim 1, wherein the determined multiple different regions of the thin section and the characteristics of the segmented grains are used to evaluate a quality of a reservoir.

10. A system, comprising:
a data processing apparatus; and
a non-transitory computer readable storage medium in data communication with the data processing apparatus storing instructions executable by the data processing apparatus and that upon such execution causes the data processing apparatus to perform operations comprising:
determining a first image of a petrographic thin section of a rock sample;
determining a feature vector for each pixel of the first image, wherein the feature vector of each respective pixel is determined based at least on color characteristics of the respective pixel;
determining multiple different regions of the petrographic thin section by clustering the pixels of the first image based on the feature vectors of the pixels of the first image over a plurality of clustering iterations using an iterative clustering technique, wherein one of the regions is a grain region that corresponds to grains in the petrographic thin section; and
determining a second image of the petrographic thin section, comprising:
combining images of the petrographic thin section acquired with plane-polarized light and cross-polarized light;
segmenting multiple grains from the second image of the petrographic thin section based on the multiple different regions from the first image, comprising:
generating a mask image based on the multiple different regions from the first image, wherein: (i) pixels of the mask image that are included in the grain region have a first predetermined value, and (ii) pixels of the mask image that are not included in the grain region have a second, different predetermined value;
highlighting the grain region in the second image by applying the mask image to the second image; and
after applying the mask image to the second image, segmenting multiple grains from the second image using a segmentation algorithm; and
determining characteristics of the segmented grains.

11. The system of claim 10, wherein the multiple different regions of the petrographic thin section correspond to at least one of grains, pores, clays, or iron oxides.

12. The system of claim 11, further comprising determining relative proportions of the multiple different regions of the petrographic thin section.

13. The system of claim 10, wherein the characteristics of the segmented grains include, for each of the multiple grains, at least one of area, perimeter, long axis diameter, short axis diameter, or roundness.

14. The system of claim 10, wherein clustering the pixels of the first image comprises applying a k-means clustering algorithm to the pixels of the first image.

15. The system of claim 10, wherein the multiple grains are segmented using a watershed segmentation algorithm.

16. The system of claim 10, wherein the determined multiple different regions of the thin section and the characteristics of the segmented grains are used to evaluate a quality of a reservoir.

17. A non-transitory computer readable storage medium storing instructions executable by a data processing apparatus and that upon such execution causes the data processing apparatus to perform operations comprising:
determining a first image of a petrographic thin section of a rock sample;
determining a feature vector for each pixel of the first image, wherein the feature vector of each respective pixel is determined based at least on color characteristics of the respective pixel;
determining multiple different regions of the petrographic thin section by clustering the pixels of the first image based on the feature vectors of the pixels of the first image over a plurality of clustering iterations using an iterative clustering technique, wherein one of the regions is a grain region that corresponds to grains in the petrographic thin section; and
determining a second image of the petrographic thin section, comprising:
combining images of the petrographic thin section acquired with plane-polarized light and cross-polarized light;
segmenting multiple grains from the second image of the petrographic thin section based on the multiple different regions from the first image, comprising:
generating a mask image based on the multiple different regions from the first image, wherein: (i) pixels of the mask image that are included in the grain region have a first predetermined value, and (ii) pixels of the mask image that are not included in the grain region have a second, different predetermined value;
highlighting the grain region in the second image by applying the mask image to the second image; and
after applying the mask image to the second image, segmenting multiple grains from the second image using a segmentation algorithm; and
determining characteristics of the segmented grains.

18. The medium of claim 17, wherein the multiple different regions of the petrographic thin section correspond to at least one of grains, pores, clays, or iron oxides.

19. The medium of claim 18, further comprising determining relative proportions of the multiple different regions of the petrographic thin section.

20. The method of claim 1, wherein applying the mask image to the second image comprises, for each pixel of the second image:
determining a product of a value of the pixel of the second image and a value of a corresponding pixel in the mask image; and
setting the value of the pixel of the second image to be a result of the product.

* * * * *